United States Patent
Muñoz Montano

(10) Patent No.: US 9,211,316 B2
(45) Date of Patent: Dec. 15, 2015

(54) COLLAGENASE G AND COLLAGENASE H COMPOSITIONS FOR THE TREATMENT OF DISEASES INVOLVING ALTERATIONS OF COLLAGEN

(75) Inventor: Juan Ramón Muñoz Montano, Madrid (ES)

(73) Assignee: PROTEOS BIOTECH S.L.U., Albacete (ES)

( * ) Notice: Subject to any disclaimer, the term of this patent is extended or adjusted under 35 U.S.C. 154(b) by 241 days.

(21) Appl. No.: 13/876,674

(22) PCT Filed: Sep. 30, 2011

(86) PCT No.: PCT/EP2011/004890
§ 371 (c)(1),
(2), (4) Date: Jun. 10, 2013

(87) PCT Pub. No.: WO2012/041512
PCT Pub. Date: Apr. 5, 2012

(65) Prior Publication Data
US 2013/0287759 A1    Oct. 31, 2013

(30) Foreign Application Priority Data
Sep. 30, 2010  (ES) .................................. 201001255

(51) Int. Cl.
| | |
|---|---|
| *A61K 38/46* | (2006.01) |
| *C12N 9/50* | (2006.01) |
| *A61K 38/48* | (2006.01) |
| *A61K 9/00* | (2006.01) |
| *A61K 9/06* | (2006.01) |
| *A61K 9/19* | (2006.01) |
| *A61K 47/36* | (2006.01) |

(52) U.S. Cl.
CPC ........... *A61K 38/4886* (2013.01); *A61K 9/0019* (2013.01); *A61K 9/06* (2013.01); *A61K 9/19* (2013.01); *A61K 47/36* (2013.01)

(58) Field of Classification Search
CPC ................................................ A61K 38/4886
USPC ............................... 424/219, 94.67; 435/219
See application file for complete search history.

(56) References Cited

U.S. PATENT DOCUMENTS

| | | | |
|---|---|---|---|
| 5,830,741 A | 11/1998 | Dwulet et al. | |
| 5,989,888 A | 11/1999 | Dwulet et al. | |
| 8,715,985 B2 * | 5/2014 | Bertuzzi et al. | ............... 435/183 |
| 8,900,576 B2 * | 12/2014 | Vaccaro et al. | ............ 424/94.67 |
| 2008/0233614 A1 * | 9/2008 | Cranenburgh et al. | ....... 435/69.1 |

FOREIGN PATENT DOCUMENTS

| | | |
|---|---|---|
| EP | 1932536 A2 | 6/2008 |
| WO | 2007089851 A2 | 8/2007 |

OTHER PUBLICATIONS

Hurst M.D., Lawrence C., et al.; "Injectable Collagenase Clostridium Histolyticum for Dupuytren's Contracture," The New England Journal of Medicine, 2009, pp. 968-979, vol. 361.
Jordan, Gerald H.; "The Use of Intralesional Clostridial Collagenase Injection Therapy for Peyronie's Disease: A Prospective, Single-Center, Non-Placebo-Controlled Study," Journal of Sexual Medicine, 2008, pp. 180-187, vol. 5.
Kin, Tatsuya, et al.; "Detrimental effect of excessive collagenase class II on human islet isolation outcome," Transplant International, 2008, pp. 1059-1065, vol. 21.
Lee, Fan, et al.; "An injectable hyaluronic acid-tyramine hydrogel system for protein delivery," Journal of Controlled Release, 2009, pp. 186-193, vol. 134.
Roche; "Liberase Research Grade Purified Enzyme Blends," www.roche-applied-science.com, Version 4, pp. 1-16, Mar. 2011.
International Search Report, Jan. 2, 2012.

* cited by examiner

*Primary Examiner* — Tekchand Saidha
(74) *Attorney, Agent, or Firm* — Tristan A. Fuierer; Moore & Van Allen, PLLC

(57) ABSTRACT

Compositions comprising collagenase G and collagenase H (in a ratio between 1:2.5 and 1:3.5), optionally formulated in hydrogels, and its uses as medicament for the treatment of diseases involving alterations of collagen, such as fibromatosis, palmar Dupuytren's contracture, La Peyronie's disease, Ledderhose's disease or retractable scars.

20 Claims, 3 Drawing Sheets

Injection sites in whole chicken legs

COLLAGENASE G AND COLLAGENASE H COMPOSITIONS FOR THE TREATMENT OF DISEASES INVOLVING ALTERATIONS OF COLLAGEN

CROSS-REFERENCE TO RELATED APPLICATIONS

This application is filed under the provisions of 35 U.S.C. §371 and claims the priority of International Patent Application No. PCT/EP2011/004890 filed on 30 Sep. 2011 entitled "Collagenase G and Collagenase H Compositions for the Treatment of Diseases Involving Alterations of Collagen" in the name of Juan Ramón MUÑOZ MONTANO, which claims priority to Spanish Patent Application No. P2010001255, filed on 30 Sep. 2010, both of which are hereby incorporated by reference herein in their entirety.

The following invention covers the fields of molecular biology, biotechnology and medicine and is related to the utilization of Collagenase G and Collagenase H for the treatment of diseases involving alterations of collagen, and the formulations containing such enzymes. In particular, it refers to the utilization of these two enzymes in a proportion of Collagenase G and Collagenase H in a ratio 1:2.5 and 1:3.5, preferably 1:3 and its sequential usage, administering first Collagenase G and then Collagenase H, or in a simultaneous utilization using a controlled release system based on a hyaluronic acid gel.

BACKGROUND OF THE INVENTION

Collagen is the main structural component in mammals and constitutes a large proportion of the total protein content of the skin and other body areas. Numerous trauma events in the skin, such as burns, surgery, infections and accidents, are frequently characterized by an abnormal accumulation of fibrous tissue rich in collagen and by a high content in proteoglycans. In addition to act repairing normal tissue that has been destroyed or damaged, Collagen also accumulates abnormally forming fibers, scars and cords that in certain conditions may produce some malformations (contractures, retractable scars). Excess of collagen has been attributed to an unbalance between synthesis and degradation of collagen.

Numerous diseases and pathologies are associated with deposits of excess of collagen and abnormal accumulation of fibrous tissue rich in collagen. Such diseases and pathologic conditions have been named collectively as "diseases involving alterations of collagen". Collagenases have been used to treat such disorders involving alterations of collagen.

Collagenases are proteolytic enzymes that bind and cut specifically to sequences containing amino acids Pro-X-Gly-Pro, where X is usually a neutral amino acid. These sequences are frequently found in collagen and very rarely found in other proteins, explaining the high substrate specificity of these enzymes. Additionally, as other enzymes are able to degrade denatured collagen, collagenases are the only enzymes able to specifically recognize native collagen and hydrolyze it (Seifter y Harper, 1970. *Methods Enzymol.* 19, 613-635; Harper, 1980. *Ann. Rev. Biochem.* 49, 1063-1078; Peterkofsky 1982. *Methods Enzymol.* 82, 453-471).

Nowadays, treatment of the diseases related to collagen is performed by using a combination of collagenase G and H in a 1:1 ratio, such enzymes are produced by fermentation of *Clostridium histolyticum* and chromatographically purified, (WO2007/089851A3). Some of such diseases related to aberrant accumulation of collagen are Dupuytren's disease (US005589171A) and ophthalmic diseases (U.S. Pat. No. 4,174,389).

In all cases, the utilization of these enzymes is presented as a mixture of Collagenases (Col I and Col II or Col G and Col H). This is because until today, the procedures to obtain these enzymes have been by purification from total cell culture supernatant or milieu form *Clostridium histolyticum* fermentation. In the total culture milieu of such fermentations both ColG and ColH are obtained at the same time in a proportion 1:1. In further steps of purification using chromatography a mixture of both enzymes ColG and ColH is obtained in order to be used as a drug, such is the case of Xiaflex, the first medicament based on collagenases that has been approved by the FDA to treat Dupuytren's contracture.

Xiaflex is presented as a lyophilized powder, which needs to be reconstituted in a solvent just prior to its utilization. The dose is 0.58 mg by injection in a palpable metacarpophalangeal or intraphalangeal cords, administered every 2 hours into 3 slightly different positions within the cord, up to 3 times per cord at 4 week intervals.

Xiaflex contains Collagenase AUX-I and Collagenase AUX-II, isolated and purified from *Clostridium histolyticum* fermentation milieu.

Collagenase AUX-I is a single chain of amino acids with observed molecular weight of 114 Kilo Daltons (kDa). It belongs to class I collagenases from *Clostridium histolyticum*.

Collagenase AUX-II is a single chain polypeptide with an observed molecular weight of 113 kDa. It belongs to class II collagenases from *Clostridium histolyticum*.

These treatments, however, have limitations derived from the nature of the final product (an aqueous solution of reconstituted collagenases AUXI and AUXII), the source of these enzymes (*C. hystoliticum*) and the combination of these collagenases G and H in a proportion 1:1. All these factors make of the current medicament a product whose activity is difficult to control, also due to the way it is released in the affected area, being its main secondary effects:

1. Normal tendon rupture in the area of treatment.
2. Serious damage in the ligaments of the fingers to be treated.
3. Allergic reactions derived from the penetration of the product into the blood stream.
4. Coagulation problems derived from the disruption of the basal membranes of blood vessels.
5. CRPS (complex regional pain syndrome),
6. Peripheral edema.
7. Pain and bruises.

These secondary effects are derived mainly from the invasion into the surrounding areas of the injection of an aqueous solution of collagenases. The aqueous solution once injected, could diffuse freely to adjacent areas producing the degradation of healthy tendons, producing immobility of joints and even reaching up to the rupture of healthy tendons and the rupture of nearby blood vessels, creating internal hemorrhagic events that are painful to the patient and invasion of the pharmacological product into the blood flow, producing important allergic reactions.

It is necessary therefore, to find a medicament, another pharmaceutical alternative that would allow obtaining the same results without the secondary effects observed with the current medicaments.

DESCRIPTION OF THE INVENTION

Composition of the Invention

The authors of the present invention have developed a composition comprising Collagenase G (ColG or AUX-I) and Collagenase H (ColH or AUX-II), being these collagenases preferably recombinant enzymes (rColG y rColH), in a precise proportion that show the best synergic activity. Such compositions, additionally, may be formulated as a gel, in order to have certain advantages, such as reduction of the dose (amount of enzymes) needed, an increased efficacy of the compositions in the area of treatment, the reduction of the typical secondary effects observed in other formulations containing collagenases, the improvement of the stability of the medicament and then the reduction in the number of administrations needed to obtain the desired therapeutic effect.

Therefore, a first aspect of the invention is related to a composition, hereinafter composition of the invention, that comprises collagenase G and collagenase H in a ratio between 1:2 and 1:4. In other words, the composition of the invention has between two to four times more collagenase H than collagenase G, that is, the mass ratio of the collagenases is between 1:2 and 1:4 (G/H)

As it is shown in FIG. 1, the enzymes collagenases, when administered in a composition in such proportions, show a strong synergic effect. This synergic effect is explained because of the nature of each one of these enzymes. Native collagen fibers are resistant to enzymatic hydrolysis because they have poor exposed surface. It is because of this reason that for an initial phase of hydrolysis it is required an enzyme with high affinity on native collagen, such as Collagenase G. This collagenase has two specific regions for collagen binding (FIG. 2), that makes it essential in a first phase of hydrolysis.

Once the collagen fiber is partially hydrolyzed, the fiber is more susceptible to be hydrolyzed by other collagenolytic enzymes more active but less specific such as the case of Collagenase H. Collagenase H shows the highest activity (FIG. 1) but lesser affinity to collagen because it has only one collagen binding domain (FIG. 2). It is because of this reason that the conjoint utilization of ColG and ColH shows a synergic effect.

The utilization of different proportions (ColG/H 1:2-1:4) than those observed in nature (ColG/H 1:1) has demonstrated to have higher efficacy in the hydrolysis of collagen fibers. In a further step, as the specific surface of collagen is increased, the action of ColH is more efficient due to its higher specific activity (FIG. 3).

In a preferred embodiment, Collagenase G and Collagenase H in the composition of the invention are found in a ratio between 1:2.5 and 1:3.5. In a more preferred embodiment, collagenase G and Collagenase H of the composition of the invention are found in a ratio 1:3 (FIG. 3).

As it was described, in general terms, commercial collagenolytic enzymes are produced from bacteria of the genus *Clostridium*. However, the recombinant production of such collagenolytic enzymes show a series of advantages, such as the possibility to produce the enzymes Collagenase G and Collagenase H separately, and in this way to adequate their concentrations, as well as to allow the utilization of Collagenase G and H in a sequential way in the treatment of the diverse diseases and the possibility to make a differential follow up of the behavior of both proteloytic enzymes once injected in the organism, either through the usage if internal markers or because the administration of each collagenase separately.

In nature, collagenases G and H are produced in the same amounts, that implicate a series of difficulties if we want to obtain proportions of a desired ratio. The main reason is that is difficult to separate collagenase G and H due to their high similarity between them. Purification is performed by size exclusion chromatography, cationic and anionic exchange.

The enzymes obtained in this way show an activity around 500 CDUs/mg and impurities measured in caseinase activity around 50 U/mg.

In a preferred embodiment, the composition of the invention is a pharmaceutical composition. In another preferred embodiment, the composition of the invention also contains a pharmaceutically acceptable carrier. In still another more preferred embodiment of the invention, the composition of the invention also contains another active ingredient.

Another aspect of the invention refers to the use of the composition of the invention in the manufacture of a medicament, or alternatively, to the composition of the invention for use as a medicament.

Kit of Parts of the Invention

In another aspect of the invention it is described a kit of parts (hereinafter kit of parts of the invention) comprising at least collagenase G and collagenase H in a ratio between 1:2 and 1:4. In a preferred embodiment, Collagenase G and Collagenase H in the kit of parts of the invention are found in a ratio between 1:2.5 and 1:3.5. In a more preferred embodiment, collagenase G and Collagenase H in the kit of parts of the invention are found in a ratio 1:3. In another preferred embodiment, the kit of parts of the invention is a pharmaceutical kit of parts.

In another preferred embodiment, the kit of parts of the invention also contains a pharmaceutically acceptable carrier. In still another more preferred embodiment of the invention, the composition of the invention also contains another active ingredient The kit of parts may comprise separate formulations of Collagenase G and Collagenase H. The separate formulations of Collagenase G and Collagenase H may be administered sequentially, separately and/or simultaneously (optionally repeatedly). Thus, the two active ingredients can be administered either as a part of the same pharmaceutical composition or in separate pharmaceutical compositions. Collagenase G can be administered prior to, at the same time as, or subsequent to administration of Collagenase H, or in some combination thereof. In a preferred embodiment, Collagenase G is administered before Collagenase H.

Pharmaceutical Form of the Invention

Another aspect of the invention refers to a pharmaceutical form, hereinafter pharmaceutical form of the invention, comprising any one of the compositions or kit of parts of the invention. In a preferred embodiment, the pharmaceutical form of the invention is selected from the list comprising: dressing, ointment, cream, paste, solution, suspension, emulsion, lotion, liniment, gel, foam, powder, or any of these forms combined.

The use of hydrogels coupled with the enzymes allows the controlled release of the active ingredient and with this lower the secondary effects because of the action of the enzymes in surrounding tissues to the area of treatment. In consequence, in another preferred embodiment of the invention, the pharmaceutical form is a gel, and in a still more preferred embodiment of the invention, are a hydrogel and/or a gel of hyaluronic acid. As used herein, the term "pharmaceutical form" preferably refers to the mixture of one or more active ingredients with or without additives that show physical characteristics for the adequate dose, conservation, administration and bioavailability.

Hydrogels are polymeric materials intertwined in a tridimensional net either from natural origin or synthetic, that increases in size when is put in contact with water forming a soft and elastic material, and that keeps a significant part of the hydrogel without dissolving it. Gels are classified in two types, concerning the nature of the bonds in a tridimensional net: physical gels and chemical gels.

Collagenases are extremely unstable proteins in aqueous solutions, even at low temperatures, and also they can easily denatured by chelating agents and various metallic ions that can interact with the Calcium ion that is essential to the enzymatic activity. Also, these enzymes are extremely sensitive to physicochemical procedures such as freezing, thawing, lyophilization and drying, processes that are usually needed during the preparations of the final formulations or pharmaceutical forms.

The authors of the present invention have developed a new formulation of the enzymes Collagenase G and Collagenase H in a gel of hyaluronic acid, in such way to obtain enzyme concentrations between 500 to 3,000 CDU/mg in hyaluronic acid, such concentrations are necessary to ensure efficient activity on tendons, and in which the enzymes are not easily denatured and affront better the physicochemical changes. Also, it has been shown the role of hyaluronic acid controlling keratinocyte proliferation and in the deposit of collagen in wounds, reducing the formation of fibrotic tissue and in consequence pathological wound healing (John Chen W. Y. et al., 1997. Wound Repair and Regeneration 7:79-89).

In consequence, another aspect of the invention refers to a hyaluronic acid gel comprising the composition of the invention. In a preferred embodiment, the concentrations of hyaluronic acid in the gel of the invention range between 0.05% to 4% (weight/weight or w/w). In a more preferred embodiment, the concentration of hyaluronic acid in the gel of the invention is 1.5% w/w.

In another preferred embodiment of the invention, the concentrations of collagenases are higher than 400 CDU/mg, in a more preferred embodiment range between 450 to 5,000 CDU/mg of hyalurionc acid, and in a still more preferred embodiment range between 500 and 3,000 CDU/mg of hyaluronic acid.

Hyaluronic acid molecular weight depends, among other factors, from the source from where is obtained (for instance, including but not limited from: synovial liquid, umbilical cord, skin, bacteria through fermentation process, or direct isolation), reaching up to 5,000 kDa (Milas et al., 2001. *Biopolymers* 59: 191-204).

Then, in another preferred embodiment, the molecular weight of the hyaluronic acid range between 600 and 4,000 kDa, and even more preferably between 700 and 3,000 kDa. In preferred particular embodiment of the invention, the hyaluronic acid has a molecular weight of 850 kDa.

Are equivalent also any gel created with similar consistence employing hyaluronic acid with higher or lower molecular weights and concentrations in aqueous solutions ranging between 0.05% to 4%. Then, they can be used derivatives of hyaluronic acid, among them and not excluding others, hyaluronic acid salted with organic and or inorganic bases (EP0138572 B1), esters of HA with alcohols of the series aliphatic, araliphatic, cycloaliphatic, aromatic, cyclic or heterocyclic, with a percentage of amidation between 1 to 10% and preferably 4% (EP 1095064 B1); derivatives of O-sulfates of HA until $4^{th}$ grade of sulphation (EP0702699 B1); internal esters of HA with a percentage of internal esterification between 0.5 to 10% and preferably 5% (EP 0341745 B1); derivatives of deacetylation of the fraction of N-acetyl-glucosamine with a percentage of deacetylation preferably between 0.1 to 30%, while all carboxyl groups of the HA could be salted with organic or inorganic bases (patent EP1313772 B1); percarboxylated derivatives of HA obtained from the oxidation of the primary hydroxyl group of the fraction N-acetyl-glucosamine with a degree of percarboxylation between 0.1 to 100% and preferably between 25 and 75%. All carboxyl groups of the HA could be salted with organic and/or inorganic bases (EP1339753).

Density of hyaluronic acid has to be enough to allow the local treatment and continuous and controlled release of the active ingredient, the collagenases. The optimal density of the gel with hyaluronic acid of 850 kDa and collagenases, is obtained with concentrations of hyaluronic acid of 1.5%, which allows to obtain an adequate consistence for injection in collagen fibers, keeping locally the active ingredient and allowing its controlled release in the area of administration. Then, in invention particular embodiment, when the molecular weight of the hyaluronic acid is 850 kDa, the concentration of this hyaluronic acid in the gel is of 1.5% w/w.

The characteristics of the hyaluronic acid in the gel will allow its lyophilization to preserve the active ingredient during the time. Also, once lyophilized the hyaluronic acid needs to be reconstituted in water to obtain a gel with a consistence similar to the initial one.

For the treatment of the diseases derived from the aberrant formation of collagen, preferably it will be used in doses that vary between 2,000 to 8,000 CDUs depending on the severity of the disease. Preferably the dose will be between 3,000 and 7,000 CDUs, and more preferably is approximately 4,000 CDUs, depending on the severity of the disease. The amount in mg needed to formulate a dose of 4,000 CDUs are directly related with the units in CDUs/mg of each batch, so it would be necessary always to refer to the amount in units rather than in mg of enzyme. Taking into account that the average activity of the enzymes is 3,500 CDU/mg in different batches, the amount in mg needed to each dose would be around 1.1 mg per dose of 4,000 CDUs (4,000 CDUs are equivalent to 13,300 ABC units).

CDU definition: One unit of collagenase is defined as the amount of enzyme that hydrolyzes 1 nmol of PZ-Pro-Leu-Gly-Pro-D-Arg in one second at pH=7.1 at 37° C. (PZ=4-phenyl-azobencyloxycarbonyl) (Wunsch et al., 1963. *Physiol. Chem.*, 333:149-151).

Uses of the Compositions, Kit of Parts, and Pharmaceutical Forms of the Invention The authors of the present invention have demonstrated that the compositions, the kit of parts, and pharmaceutical forms of the invention, including the hydrogels of hyaluronic acid (or its derivatives), comprising the proportions of collagenase G and collagenase H previously described, are useful for the treatment of diseases related to aberrant malformations of collagen.

Therefore, another aspect refers the use of the composition of the invention, or the use separately, simultaneous or sequential of the active ingredients (collagenase G and collagenase H) of the kit of parts of the invention, or to the use of the pharmaceutical form of the invention, in the manufacture of a medicament. Alternatively, it refers to the composition of the invention, the kit of parts of the invention, or to the pharmaceutical form of the invention, for its use in the manufacture of a medicament. In a preferred embodiment, the pharmaceutical form of the invention is a hydrogel of hyaluronic acid such as it has been defined previously.

Another aspect refers to the use of the composition of the invention, the use separately, simultaneous or sequential of the active ingredients (collagenase G and collagenase H) of the kit of parts of the invention, or to the use of the pharmaceutical form of the invention, in the manufacture of a medicament for the treatment of diseases related to disorders in connective tissue, or alternatively, to the composition of the invention, the kit of parts of the invention or the pharmaceutical form of the invention, for use in the treatment of diseases related to disorders in connective tissue.

In a preferred embodiment of the invention, the disease that is related to disorders in connective tissue is a fibromatosis. In a preferred aspect of the invention, fibromatosis is selected from a list of disorders that include: Dupuytren's palm contracture, Peyronie's disease, Ledderhose disease or plantar fascial fibromatosis, or the existence of fibrous tissue in the ear lobe, or the fibrosis caused by surgical interventions or accidents called retractable scars.

The diseases related to alterations in the collagen are easily identified by clinical diagnosis and, if necessary, through histological evidence. Then, for instance, Dupuytren's contracture is diagnosed by a physician during physical examination of the affected hand.

DEFINITIONS

As it used here, the terms "active ingredient", "active substance", "active pharmaceutical substance", "active principle" or "active pharmaceutical ingredient" means any component that potentially provides a pharmacological activity or another different effect in the diagnosis, cure, mitigation, treatment or prevention of a disease, or that affect the structure and function of the human body and of other animals. The term includes those components that promote a chemical change in the elaboration of the medicament and that are present in the same in a predicted modified form that provides the specific activity or the effect.

Either compositions of the present invention, as well as the kit of parts, can be formulated for its administration in an animal and more preferably in a mammal, including humans, in a variety of forms known in the state of the art. Therefore, they can be included, but not limited to, sterile aqueous solution or in biological fluids, such as serum. The aqueous solutions could be buffered or not and they can contain other active or inactive ingredients as well. The additional components include salts to modulate ionic strength, preservatives, including but not limited to, antimicrobial agents, antioxidants, chelating agents and similar, and nutrients including glucose, dextrose, vitamins and minerals. Alternatively, the compositions may be prepared for its administration in solid form. Compositions can be combined with other various vehicles or inert excipients, including but not limited to: agglutinating agent such as microcrystalline cellulose, tragacanth, gelatin; excipients such as starch or lactose; dispersant agents such as alginic acid of maize starch; lubricants such as magnesium stearate; gliding agents such as colloidal silicon dioxide; sweetener such as sucrose or saccharine; or aromatic agents such as mint or methyl salicylate.

The term "medicament", as it is used in this report, makes reference to any substance used for prevention, diagnosis, relief, treatment or cure of diseases in humans and animals. In the context of the present invention, the disease is a disease that is related to alterations on the connective tissue, preferably it is a fibromatosis, and more preferably in a palmar Dupuytren's contracture, Peyronie's disease, Ledderhose's disease or plantar fascial fibromatosis, or retractable scars.

Such compositions or combined preparations and/or its formulations may be administered in an animal, including a mammal and therefore humans, in a variety of forms, including but not limited to, intraperitoneal, intravenous, intramuscular, subcutaneous, intrathecal, intraventricular, oral, enteral, parenteral, intranasal or topic.

The dose to obtain an amount therapeutically effective depends on a variety of factors, such as for instance, age, sex, weight, tolerance of the mammal. In the sense used in this description, the term "amount therapeutically effective" refers to the amount of collagenase G and collagenase H that produce the desired effect and in general it is determined among other factors, by the intrinsic characteristics of the prodrug, derivatives or analogs and by the therapeutic effect to be obtained. The "adjuvant" and "vehicles pharmaceutically acceptable" that could be used in such compositions are well known vehicles in the field.

All enzymes (collagenase G and collagenase H) have a 6 histidine tag that allows to combine them into the hydrogels, such as the hyaluronic acid. The 6 histidine tag allows also to purify the enzymes using nickel affinity chromatography. Furthermore, the detection of the presence of collagenases in the blood stream or in adjacent tissues can be realized using immunoassays (for instance but not limited to ELISA). To do so, specific antibodies against clostridial collagenases are used, although they do not distinguish between collagenase G and collagenase H. In addition, the collagenases in the medicament have a 6-histidine tag, the enzymes can also be recognized both with specific antibodies against the collagenases and against the 6-histidine tag.

In this report, we understand as disorders of the connective tissue to diseases related to subdermic accumulation of this type of tissue.

The term fibromatosis refers to a group of tissues which usually form benign tumors, they are characterized by the absence of cytological and clinical malignancy. It is also distinguished by the proliferation of fibroblasts a growth structure of the type infiltrative and an aggressive clinical behavior with frequent recurrency. Fibromatosis includes diverse subtypes: juvenile fibromatosis, fibromatosis colli, infantile digital fibromatosis, infantile myofibromatosis, ipofibromatosis, fibromatosis hyalinica multiplex, plantar fibromatosis, Peyronie's disease and Dupytren's disease.

Dupuytren's disease (also called Dupuytren's contracture or palmar Dupuytren's contracture) consists in a retraction of the palm with the situation where certain fingers cannot bend; it usually begins with a skin enlargement observed in the palm which could evolve into a strong bump of thick cord.

Peyronie's disease or induratio penis plastic is a process of unknown causes characterized by the presence of an abnormal fibrous band in the of the tunica albuginea of the cavernous bodies of the penis. It is usually unilateral and it has as main consequence a curvature of the penis during erection. Depending of the extension of this fibrous band, the process could prevent or make penetration difficult, or produce pain during erection.

Ledderhose's disease also known as Morbus Ledderhose, plantar fibromatosis, and plantar aponeurosis is a relatively rare condition it is a non-malignant thickening of the feet's deep connective tissue, or fascia. At the beginning, nodules or cords start growing along tendons of the foot, the disease is considered minor, but can be painful. Eventually, however, the cords thicken, the toes stiffen and bend, and walking becomes painful. As most of fibromatosis it is non malignant and it evolution varies depending on each patient. Nodules are typically of a slow growth and mostly found in central or medial portions of the plantar fascia. Sometimes the nodules may be inactive for months or even years, to suddenly begin a fast growth and in an unexpected way. Only solution is surgery if the pain impedes walking.

Collagenase G one of the examples of the invention posses a sequence of 3,357 nucleotides (SEQ ID NO: 3). The first 330 nucleotides code for the signal peptide (SEQ ID NO: 4) the first amino acid of the mature secreted form of the protein is encoded by an ATA codon. The presence of the signal peptide and its processing ensure the correct folding of the final active nature form of the enzyme. In the case of the recombinant collagenase G a sequence coding for 6-histidine codons is added before the last codon (stop codon). This 6-histidine tag is necessary for purification purposes and to immobilize the enzyme in the pharmaceutical forms.

The amino acid sequence is composed by 1,118 amino acids. The 110 amino acids of the extreme N-terminus constitute the signal peptide (SEQ ID NO: 5) and the remaining 1,008 amino acids corresponds to the secreted collagenase (SEQ ID NO: 1).

The collagenase G with signal peptide used in this invention has the following physicochemical parameters:
  Molecular weight: 127 kDa.
  Isoelectric point: 5.8
  Number of negative charges (Asp+Glu): 160.
  Number of positive charges (Arg+Lys): 142.
  Theoretical index of instability: 26.61, which classify the protein as stable.
  Theoretical half-life estimated in *Escherichia coli* (in vivo): more than 10 hours.

The collagenase G without signal peptide has the following physicochemical parameters:
  Molecular weight: 114.8 kDa.
  Isoelectric point: 5.53
  Number of negative charges (Asp+Glu): 145.
  Number of positive charges (Arg+Lys): 122.
  Theoretical index of instability: 24.11, which classify the protein as stable.
  Theoretical half-life estimated in *Escherichia coli* (in vivo): more than 10 hours.

Other Collagenases similar to Collagenase G in the invention could be used. Therefore, in the context of the present invention, "Collagenase G" (ColG or AUX-I) is also defined by a nucleotide or polynucleotide sequence, which constitute the coding sequence of protein "Collagenase G", and which also comprises different variants proceeding from:
  a) nucleic acid molecules encoding a polypeptide comprising the amino acid sequence of SEQ ID NO: 1,
  b) nucleic acid molecules whose complementary strand hybridizes with the polynucleotide sequence of a),
  c) nucleic acid molecules whose sequence differs from a) and/or b) due to degeneration of the genetic code, or
  d) nucleic acid molecules that encode a polypeptide comprising an amino acid sequence with an identity of at least 80%, 90%, 95%, 98% or 99% with SEQ ID NO: 1 in which the polypeptide encoded by said nucleic acid has the activity and structural characteristics of the protein "Collagenase G". The term also includes proteins resulting from post-translational modifications.

"Collagenase H" has a nucleotide sequence consisting of 3066 nucleotides (SEQ ID NO:6). The first 120 SEQ ID NO: 7) encode a signal peptide and the first amino acid of the secreted mature protein is encoded by codon GTA). The signal peptide is incorporated to allow secretion of the enzyme in the extracellular medium. Once in the bacterial membrane, the signal peptide is cut and the active enzyme is released into the medium. In the case of recombinant Collagenase H, the last codon (stop codon) is eliminated and it is replaced by a nucleotide sequence coding for 6-Histidines necessary for the subsequent process of purification or immobilization in dosage forms.

The amino acid sequence consists of 1021 amino acids. The 40 residues of the amino terminal comprising the signal peptide (SEQ ID NO: 8) and the remaining 981 for the secreted Collagenase (SEQ ID NO: 2)

Collagenase H with signal peptide has the following physicochemical parameters:
  Molecular weight: 117.2 kDa
  Isoelectric point: 5.99
  Number of negative charges (Asp+Glu): 142
  Number of positive charges (Arg+Lys): 128
  Theoretical instability index: 35.48, which classifies the protein as stable.
  Estimated theoretical half-life in *Escherichia coli* (in vivo): greater than 10 hours.

Collagenase H without the signal peptide has the following physicochemical parameters:
  Molecular Weight: 112.98 Kda
  Isoelectric point: 5.76
  Number of negative charges (Asp+Glu): 141
  Number of positive charges (Arg+Lys): 122
  Theoretical instability index: 35.30, which classifies the protein stable.
  Estimated theoretical half-life in *Escherichia coli* (in vivo): greater than 10 hours.

Other Collagenases similar to Collagenase H in the invention could be used. Therefore, in the context of the present invention, "Collagenase H" (ColH or AUX-II) is also defined by a nucleotide or polynucleotide sequence, which constitute the coding sequence of protein "Collagenase H", and which also comprises different variants proceeding from:
  a) nucleic acid molecules encoding a polypeptide comprising the amino acid sequence of SEQ ID NO: 2,
  b) nucleic acid molecules whose complementary strand hybridizes with the polynucleotide sequence of a),
  c) nucleic acid molecules whose sequence differs from a) and/or b) due to degeneration of the genetic code, or
  d) nucleic acid molecules that encode a polypeptide comprising an amino acid sequence with an identity of at least 80%, 90%, 95%, 98% or 99% with SEQ ID NO: 2. in which the polypeptide encoded by said nucleic acid has the activity and structural characteristics of the protein "Collagenase H". The term also includes proteins resulting from post-translational modifications.

Throughout the description and claims, the word "comprise" and its variants are not intended to exclude other technical features, additives, components, or steps. For those skilled in the matter, other objects, advantages and features of the invention will become apparent from the description and from the practice of the invention. The following examples and drawings are provided by way of illustration and are not intended to be limiting of the present invention.

EXAMPLES

Figure 1:
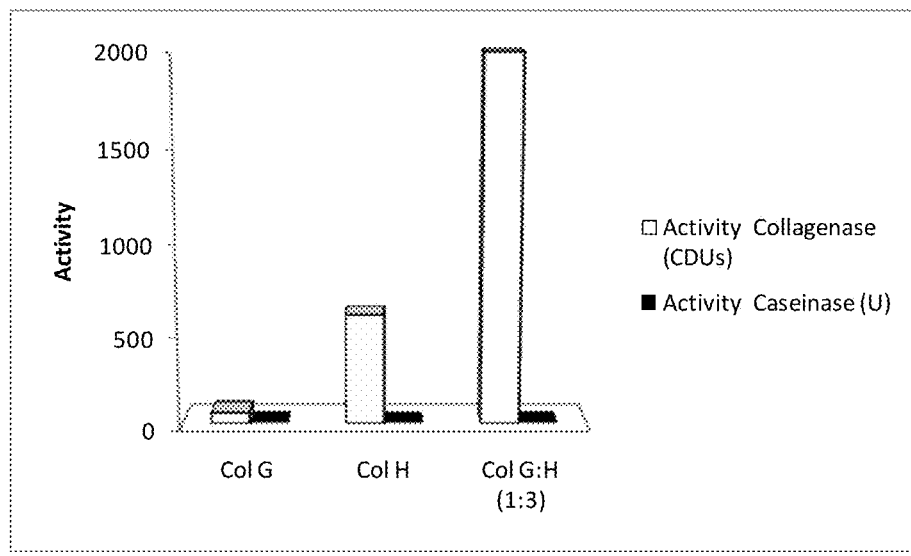
FIG. 1. Synergistic effect of the use of Collagenase G and Collagenase H in a ratio of 1:3. Activity of Collagenase G and Collagenase H separately and in combination in a 1:3 ratio.
Figure 2:
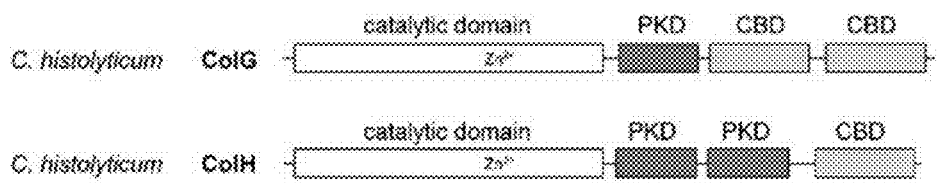
FIG. 2. Scheme of the molecular structure of Collagenase G and H. The collagenases have a common catalytic domain and collagen-binding domains (CBD). In the case of ColG this domain is repeated so that the affinity for collagen is greater.

Following comes illustrated the invention by means of tests performed by the inventors.

Example 1

Preparation and Properties of Collagenases

Collagenase H and Collagenase G are metalloproteinases (class II) which can specifically degrade collagen helical regions, recognizing the Gly-Pro-X reason characteristic to the macromolecule. These proteins have a tail of 6 Histidines at its carboxyl terminus (Demina & Lysenko. *Mikrobiologiia*. 1996 May-June; 65(3):293-304).

Isoelectric point and molecular weight: Col.H: Ip 5.76; MW 112.98 kDa; Col.G: Ip 5.53; MW 114.8 Kda.

Purity: 99.9% Purification by nickel affinity columns, ion exchange and exclusion.

It is presented as lyophilized and sterile. Deionized sterile water is used for optimal reconstitution:

Stock Preparation

For the preparation Collagenase G/H 1:3, the lyophilized presentation contains 800 CDUs (approx. 0.3 mg). For administration it is recommended to resuspend the content of the vial in 1 ml sterile mQ water to obtain a solution of the enzyme 800 CDUs/ml in 20 mM Tris buffer pH 8.0. It is recommended to prepare this solution at the time of use.

The recommended dosage depends on the degree of progression of the disease ranging from 100-800 CDUs per application.

The recombinant collagenases G and H have no non-specific protease activity (caseinase) negative Ladd-Butler Test. They do not contain endotoxins (negative Gen Script test).

Example 2

Preparation of the Pharmaceutical Form of the Invention

Recombinant (rColG and rColH) Collagenase G (ColG or AUX-I) and Collagenase H (ColH or AUX-II), separately or combined, and more specifically in the ratio 1:3 formulated as a therapeutic gel, such as Hyaluronic acid. Hyaluronic acid is classified as a Medical Device and was produced by Novozymes Biopharma with a molecular weight of 850 kDa.

The density of the Hyaluronic acid should be sufficient so as to allow local treatment and the continuous and controlled release of the active ingredient, collagenases. The optimum density of the Hyaluronic acid gel 850 KDa with Collagenase is 1.5%, allowing a suitable consistency for the injection of collagen fibers, retaining the active ingredient locally and allowing the controlled release in the area of application.

Any other similar consistency gel made with hyaluronic acid is equivalent, using higher or lower molecular weights and concentrations of the same in aqueous solutions variable between 0.05%-4%.

The characteristics of the Hyaluronic acid gel must allow lyophilization so as to preserve the active ingredient over time. In addition, Hyaluronic acid once lyophilized must be reconstituted in water to obtain a gel consistency similar to the one at the beginning. Table 1 shows the gel's ability to rebuild its consistency after lyophilization.

Materials

Hyaluronic acid ref. NZ HA-MMW 0.85 MDa Medical device

Hyaluronic acid ref. NZ HA-HMW 1.3 MDa Medical device

PBS buffer 4 mM GIBCO™

Analytical Method (Equipment)

Brookfield Viscometer (LVDV II+Pro)

Temperature 25° C.

Geometry. Cone/plate CP 40

Analysis of molecular weight (SEC-MALS-RI)

System: Waters Alliance HPLC system and Wyatt MALS (Dawn EOS) and RI (Optilab rEX)

Software: ASTRA 5.

Columns: TSKgel PWXL guard column (4 cm×6.0 mm ID) and 2×TSKgel

G5000PWXL (30 cm×7.8 mm ID).

Standards: Ref HA, Dextran and BSA

Figure 3:
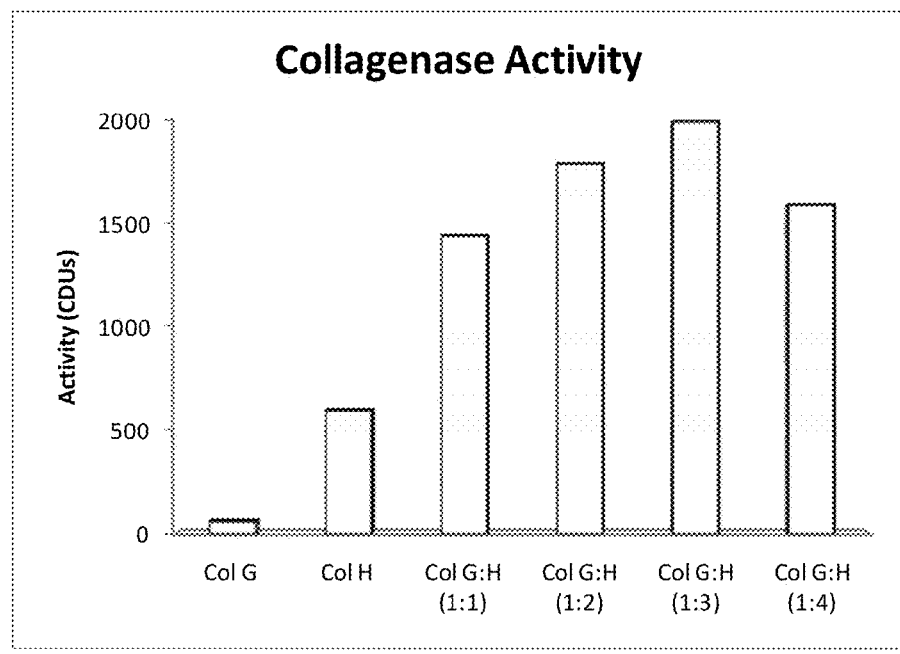
FIG. 3. Comparison of the synergistic action of collagenases. There was noted an increase of the synergistic effect by using collagenase G/H in proportions preferably 1:2-1:4 and 1:3 with an increase of over 25% of the specific activity.

The proportion of use between Collagenase G and Collagenase H is established by determining the specific activity between the two and in synergy as shown in FIG. 3. The activity of mixtures of lyophilized ColG and ColH, is done by always maintaining the same ratio of ColG and varying the proportion of ColH, which is the protein that increases the total collagenase activity. In all three trials shown, it is observed that in two of three times the optimal mix consists of 1 molecule of ColG and 3 molecules of ColH. The optimal mix of ColG/H increases the final activity more than 33 times the activity of ColG or 3 times the activity of ColH separately and more than the 25% the 1:1 mixture of ColG:ColH (FIG. 3).

The results of the reconstitution of the Hyaluronic acid with distilled water after lyophilization of the initial gel, indicates that Hyaluronic acid samples with 3000 CDUs of collagenase G/H in 1:3 ratio at concentrations of 1.0, 1.5 and 2.0% of hyaluronic acid 850 KDa and 1% of hyaluronic acid 1300 KDa in PBS buffer have different behavior as shown in the following table (Table 1):

TABLE 1

Viscosity and molecular weight of different Hyaluronic acid formulations of 850 kDa and 1300 kDa; cP (centipoise): viscosity measurement; MW (kDa): Molecular weight measurement extracted from the value of viscosity.

| Sample | Viscosity (cP) | Molecular Weight (KDa) |
|---|---|---|
| 850-1.0% | 218 | 707 |
| 850-1.5% | 3203 | |
| 850-2.0% | 5034 | |
| 1300-1.0% | 1150 | 1,339 |

After lyophilization, the samples were redissolved at 25° C. in deionized water and both molecular weight and dynamic viscosity (DV) were measured. The results are shown in the following table (Table 2):

| Sample | Viscosity | % retained viscosity | Molecular Weight (KDa) | % Retained Molecular Weight | Reconstitution Time |
|---|---|---|---|---|---|
| 850-1.0% | 249 | 114.2 | 763 | 108 | <10 min |
| 850-1.5% | 2920 | 91.2 | 780 | 110 | <15 min |
| 850-2.0% | 4542 | 90.2 | 757 | 107 | <20 min |
| 1300-1.0% | 1076 | 93.6 | 1275 | 95 | <90 min |

As noted in Table 2, both molecular weight and retained viscosity are completely recovered after lyophilization and redissolution.

Reconstitution of selected samples of 850 kDa has to be done after lyophilization, with agitation for 10-20 minutes and those of 1300 kDa with agitation for more than 90 minutes.

The above samples were analyzed by the department of Orthopaedics at the University Hospital in Albacete, who valued the consistency of the gels, the handling of the hypodermic needles (reference: hypodermic needle 13 mm length and 0.3 mm diameter), the manipulation and the tendon retention. The results are shown in the following table (Table 3):

TABLE 3

Assessment of the hydrogels.
Rating: Poor: 0-1, Medium: 2-3, Good: 4-5

| Sample | Consistency | Needle Handling | Manipulation | Tendon Retention | TOTAL VALUE |
|---|---|---|---|---|---|
| 850-1.0% | 2 | 5 | 5 | 2 | 14 |
| 850-1.5% | 5 | 4 | 5 | 5 | 19 |
| 850-2.0% | 5 | 3 | 3 | 5 | 16 |
| 1300-1.0% | 5 | 2 | 3 | 5 | 15 |

According to previous results, the ideal concentration of 1.5% was chosen as it has the highest score among the analyzed samples. However, the use of other source materials and different concentrations is not ruled out, depending on the needs observed by the physician.

The purity levels must comply with the GMP (Good Manufacturing Practices) regulation for the use of biological products for human use.

Presentation of the Final Product

The drug is presented in a powder form that has to be reconstituted in 0.450 ml in sterile borosilicate vials. Each vial contains between 2000-8000 CDUs Collagenase, preferably 4000 CDU (approx. 1.1 mg) containing ColG and ColH proteins and lyophilized Hyaluronic acid and a buffer containing 2 mM CaCl2 and 150 mM NaCl. The drug is reconstituted with sterile deionized water that comes in another separate vial. The process of reconstitution of a hyaluronic acid gel 1.5% 850 KDa involves the incubation of the lyophilized gel in sterile deionized water for 15 minutes stirring at 25° C.

The final product is a gel containing the necessary and sufficient active ingredient to treat the anomalies seen in some diseases such as Dupuytren's contracture and other similar anomalies.

For the treatment of diseases related to aberrant collagen malformation, 4000 CDUs are preferably used although the doses may vary between 2000-8000 CDUs, depending on the severity of the disease. The milligrams necessary to formulate the 4000 CDUs dose are directly related to the CDU units/mg of each batch, therefore it is necessary to always refer the doses to units of enzyme. Given that the average activity of the enzymes are 3500 CDU/mg per batch, the milligrams required for each dose would be around 1.1 mg for 4000 CDU doses (4000 CDU are the equivalent of approximately 13,300 ABC units).

Efficacy trials conducted with Collagenase G/H in a ratio of 1:3 in the presence of Hyaluronic acid 850 KDa at 1.5% in chicken tendons demonstrate the effectiveness of the gel in regards to the aqueous solution.

Example 3

Ex Vivo and In Vitro Studies of the Gel Activity on Chicken Tendons

The activity of the gel was analyzed on chicken tendon samples. Ex vivo tests were performed and tests on the effect of Collagenase over time.

The ex vivo tests on the doses to be used have been conducted on 40 chicken tendons on which over 80 results were analyzed. In regards to the tests about the effect of Collagenase on the tendons over time, we analyzed 24 tendons with a total of 7 measures for each tendon, therefore having analyzed 168 results.

Figure 4:
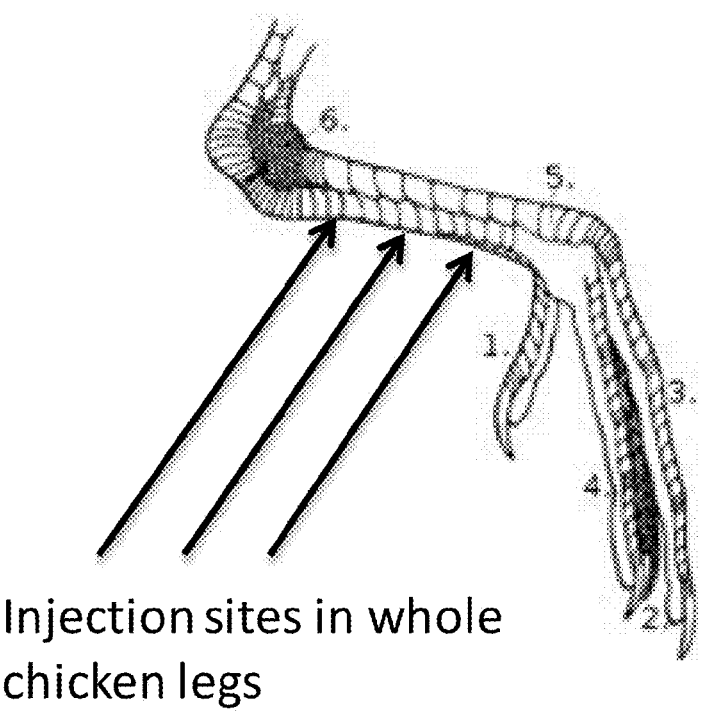
FIG. 4. Scheme of the injection of the Collagenase dose in hyaluronic acid gel in a chicken leg model.
Figure 5:
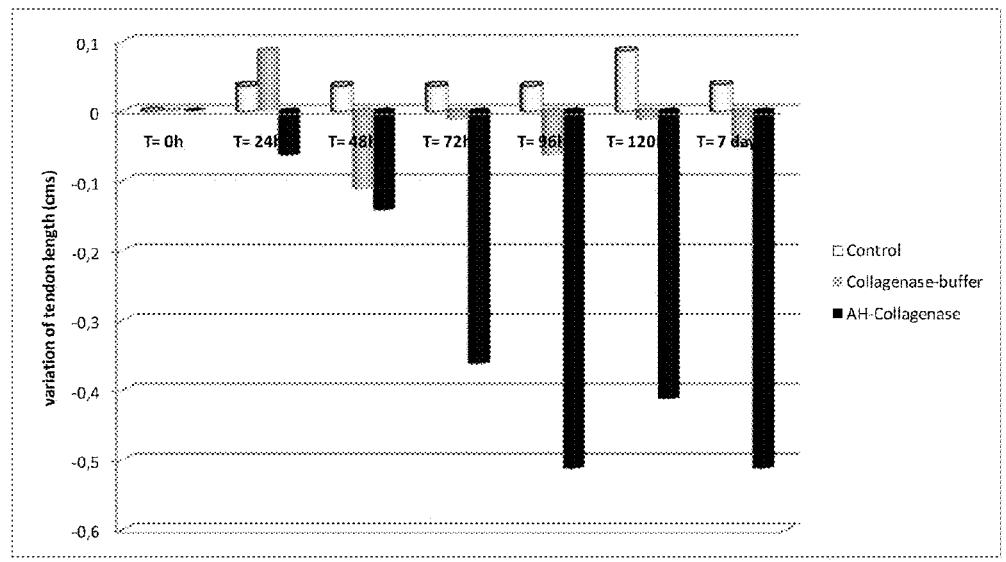
FIG. 5. Variation in the length of the tendons after the treatment with Collagenase G/H 1:3 with and without Hyaluronic acid. As shown in the graph, the effect of AH-Collagenase is perceived from the first 24 hours and there is a gradual increase until achieving reductions of more than 0.5 inches after 96 hours of treatment.
Figure 6:
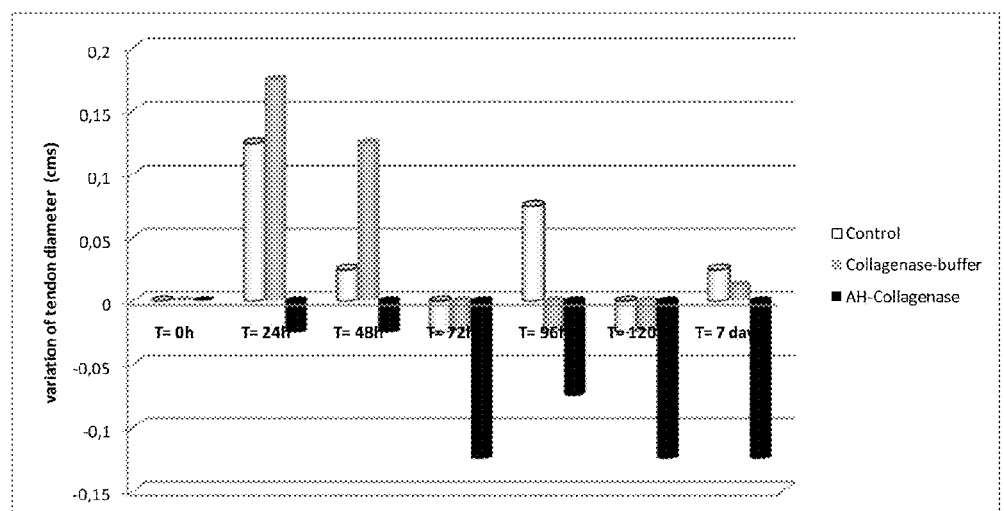
FIG. 6. Variation in the diameter of the cross section of the tendons after the treatment with Collagenase G/H 1:3 with and without Hyaluronic acid. Differential effect of Collagenase G/H 1:3 included in Hyaluronic acid gels and in aqueous solution. As shown in the graph, there is a significant effect of reducing the diameter of the section of the tendon after 24 hours of treatment. The effect of diameter increase in controls at 24 and 48 hours are due to the volume of injected aqueous solution into the tendon, which by itself increases the diameter of the tendon.

The chicken legs were injected intra-tendon in three different parts in the places shown in FIG. 4; the applied doses were 3000 CDUs in a total volume of 450 microliters of Hyaluronic acid gel (a dose is divided into these three injection sites). The applications were made in the back of the leg where the main tendons are located.

To determine the efficacy of the product, different types of in vitro testing have been conducted, such as:
Dose Determination
Histological Studies
Immunohistochemical Studies Dose Determination:

The optimum Collagenase gel application dose on tendon was determined by applying different doses on the chicken leg.

An increasing gradient of doses of Collagenase G/H in a ratio of 1:3 were applied (Table 4):

TABLE 4

| Increasing doses of Collagenase G/H in a ratio of 1:3 | |
|---|---|
| Collagenase Activity (CDU) | Application of these units to: |
| 300 | Collagenase + Hyaluronic acid |
| 1500 | Collagenase + Buffer |
| 3000 | Control buffer |
| 6000 | |
| 12000 | |

Each leg was performed a longitudinal section so as to expose the tendon and make all three injections on the tissue. Then the leg was sewed to facilitate the action of the gel Collagenase on the tissue.

The doses of Collagenase G/H 1:3 were resuspended in 50 µl of sterile water. In parallel, the corresponding amount of Hyaluronic acid was resuspended in 400 µl of sterile water so as to obtain a concentration of 1.5%. Both solutions were mixed yielding a total solution of 450 µl. On the other hand, the 50 µl dose of the corresponding enzyme was mixed with water, thus obtaining the other buffer under study.

There will be two negative controls, one where a solution of 1.5% Hyaluronic acid (450 μl) will be injected and a negative control where 450 μl of sterile water will be injected.

Samples with different doses were kept immobile and immersed in sterile PBS 1×pH 7.2 at 37° C. for 72 hours, after which effectiveness was examined.

After this period, the legs were dissected, extracted tendons were washed in PBS 1×pH 7.2. The tissue was evaluated in immunohistochemical studies which determined that the optimal dose was 3000 CDUs as shown in the following table (Table 5):

TABLE 5

Histochemical rating of the applied doses. No apparent effect: 0; Light effect: 1; Significant effect: 2; Disproportionate effect: 3.

| CDUs | Effect on the tendon | Effect over adjacent tissues |
|---|---|---|
| 300 | 0 | 0 |
| 1500 | 1 | 0 |
| 3000 | 2 | 0 |
| 6000 | 2 | 2 |
| 12000 | 3 | 3 |

After the analysis of the immunohistochemical results on the tendon and surrounding tissues, 3000 CDUs was determined to be the optimal usage dose, which yields a significant effect on the tendon and no effect on adjacent tissues.

Example 4

Determination of the Compared Effect Between Collagenase in Aqueous Solution and in Hyaluronic Acid Gel 3000 CDUs of Collagenase were used as the optimum application on tendon dose of Collagenase gel. The trial was conducted on freshly extracted tendons taken from chicken legs through surgery. All tendons were measured at the beginning of the experiment to take the control reference, because when dissecting the tendons, the presence of Collagenase does not make them break, but the effect of hydrolysis is observed in the size reduction.

Once measured, the tendons were injected with hypodermic syringes with similar amounts of 450 μl of PBS buffer, Collagenase G/H 1:3 in 1.5% 850 kDa Hyaluronic acid gel and Collagenase G/H 1:3 in PBS buffer.

The tests were performed at 24 h, 48 h, 72 h, 96 h, 180 h and 7 days. After each of these periods, the tendons variation in sizes was measured, thus obtaining a significant reduction in the case of AH-Collagenase in regards to the control and the Collagenase in solution, as shown in the following table (Table 6):

TABLE 6

Reduction of tendon size (in centimeters (cm)). The differences in regards to the control and Collagenase in aqueous solution are significant, mainly due to the dilution effect after the injection. This dilution effect is not observed in the case of the gel as it is a product with a solid structure and whose action is locally concentrated on the tendon.

| | Control-PBS | Collagenase-PBS | AH-Collagenase |
|---|---|---|---|
| T = 0 h | 0 | 0 | 0 |
| T = 24 h | 0.0375 | 0.0875 | −0.0625 |
| T = 48 h | 0.0375 | −0.1125 | −0.1625 |
| T = 72 h | 0.0375 | −0.0125 | −0.3625 |
| T = 96 h | 0.0375 | −0.0625 | −0.5125 |
| T = 120 h | 0.0875 | −0.0125 | −0.4125 |
| T = 7 days | 0.0458 | −0.05 | −0.5125 |

Also, the effect observed in the thickening of the tendon after the same previous treatment shows a reduction of cross-sectional diameter of the tendon which is significant in the case of the collagenases included in the Hyaluronic acid gel, as shown in the table below (Table 7):

TABLE 7

Variation in centimeters in the diameter of the tendons section after the treatment with Collagenase.

| | AH-Collagenase | Control | Collagenase-buffer |
|---|---|---|---|
| T = 0 h | 0 | 0 | 0 |
| T = 24 h | −0.025 | 0.125 | 0.175 |
| T = 48 h | −0.025 | 0.025 | 0.125 |
| T = 72 h | −0.125 | −0.025 | −0.025 |
| T = 96 h | −0.075 | 0.075 | −0.025 |
| T = 120 h | −0.125 | −0.025 | −0.025 |
| T = 7 days | −0.125 | 0.025 | 0.0125 |

The invention claimed is:

1. A composition comprising recombinant Collagenase G and recombinant Collagenase H having a mass ratio between 1:2.5 and 1:3.5, wherein the recombinant Collagenase G has the amino acid sequence of SEQ ID NO: 1 and the recombinant Collagenase H has the amino acid sequence SEQ ID NO: 2.

2. A kit comprising recombinant Collagenase G and recombinant Collagenase H having a mass ratio between 1:2.5 and 1:3.5, wherein the recombinant Collagenase G has the amino acid sequence of SEQ ID NO: 1 and the recombinant Collagenase H has the amino acid sequence SEQ ID NO: 2.

3. The composition according to claim 1, wherein the recombinant Collagenase G and/or recombinant collagenase H have a 6-histidine tag located at the C-terminus of their amino acid sequence.

4. The composition according to claim 1, wherein the composition is a pharmaceutical composition.

5. The composition according to claim 1, which also comprises a pharmaceutically acceptable carrier.

6. The composition according to claim 1, further comprising another active ingredient.

7. A pharmaceutical composition comprising the composition according to claim 1.

8. The pharmaceutical composition according to the claim 7 which is selected from the group consisting of: plasters, ointment, paste, cream, solution, suspension, emulsion, lotion, liniment, jelly, gel, foam, powder, and any combination thereof.

9. The pharmaceutical composition according to claim 7, comprising hyaluronic acid in concentrations of between 0.05% and 4%.

10. The pharmaceutical composition according to claim 9, wherein the hyaluronic acid is in a concentration of about 1.5%.

11. The pharmaceutical composition according to claim 9, wherein the concentrations of collagenases are higher than 400 CDU/mg of hyaluronic acid.

12. The pharmaceutical composition according to claim 9, wherein the concentrations of collagenases ranges between 450 and 5000 CDU/mg of hyaluronic acid.

13. The pharmaceutical composition according to claim 9, wherein the hyaluronic acid has a molecular weight between 500 and 5,000 kDa.

14. The pharmaceutical composition according to claim 9, wherein the hyaluronic acid has a molecular weight of approximately 850 kDa.

15. The composition according to claim 1, for use as a medicament.

16. A method for the treatment of diseases involving alterations in connective tissue or fibromatosis, said method comprising administering to a subject in need thereof a therapeutically effective amount of the kit according to claim 2.

17. A method for the treatment of diseases involving alterations in connective tissue, said method comprising administering to a subject in need thereof a therapeutically effective amount of the composition according to claim 1.

18. A method for the treatment of fibromatosis, said method comprising administering to a subject in need thereof a therapeutically effective amount of the composition according to claim 1.

19. The method according to claim 18, wherein the fibromatosis is selected from the group consisting of: palmar Dupuytren's contracture, La Peyronie's disease, Ledderhose's disease or plantar fascial fibromatosis, and retractable scars.

20. A method for the treatment of diseases involving alterations in connective tissue or fibromatosis, said method comprising administering to a subject in need thereof a therapeutically effective amount a kit according to claim 2, said method comprising administering collagenase G before or simultaneously with collagenase H.

* * * * *

SEQUENCE LISTING

<160> NUMBER OF SEQ ID NOS: 8

<210> SEQ ID NO 1
<211> LENGTH: 1008
<212> TYPE: PRT
<213> ORGANISM: Artificial Sequence
<220> FEATURE:
<223> OTHER INFORMATION: Synthetic Construct

<400> SEQUENCE: 1

Ile Ala Asn Thr Asn Ser Glu Lys Tyr Asp Phe Glu Tyr Leu Asn Gly
1               5                   10                  15

Leu Ser Tyr Thr Glu Leu Thr Asn Leu Ile Lys Asn Ile Lys Trp Asn
            20                  25                  30

```
Gln Ile Asn Gly Leu Phe Asn Tyr Ser Thr Gly Ser Gln Lys Phe Phe
                 35                  40                  45
Gly Asp Lys Asn Arg Val Gln Ala Ile Ile Asn Ala Leu Gln Glu Ser
         50                  55                  60
Gly Arg Thr Tyr Thr Ala Asn Asp Met Lys Gly Ile Glu Thr Phe Thr
 65                  70                  75                  80
Glu Val Leu Arg Ala Gly Phe Tyr Leu Gly Tyr Tyr Asn Asp Gly Leu
                 85                  90                  95
Ser Tyr Leu Asn Asp Arg Asn Phe Gln Asp Lys Cys Ile Pro Ala Met
                100                 105                 110
Ile Ala Ile Gln Lys Asn Pro Asn Phe Lys Leu Gly Thr Ala Val Gln
                115                 120                 125
Asp Glu Val Ile Thr Ser Leu Gly Lys Leu Ile Gly Asn Ala Ser Ala
        130                 135                 140
Asn Ala Glu Val Val Asn Asn Cys Val Pro Val Leu Lys Gln Phe Arg
145                 150                 155                 160
Glu Asn Leu Asn Gln Tyr Ala Pro Asp Tyr Val Lys Gly Thr Ala Val
                165                 170                 175
Asn Glu Leu Ile Lys Gly Ile Glu Phe Asp Phe Ser Gly Ala Ala Tyr
                180                 185                 190
Glu Lys Asp Val Lys Thr Met Pro Trp Tyr Gly Lys Ile Asp Pro Phe
                195                 200                 205
Ile Asn Glu Leu Lys Ala Leu Gly Leu Tyr Gly Asn Ile Thr Ser Ala
        210                 215                 220
Thr Glu Trp Ala Ser Asp Val Gly Ile Tyr Tyr Leu Ser Lys Phe Gly
225                 230                 235                 240
Leu Tyr Ser Thr Asn Arg Asn Asp Ile Val Gln Ser Leu Glu Lys Ala
                245                 250                 255
Val Asp Met Tyr Lys Tyr Gly Lys Ile Ala Phe Val Ala Met Glu Arg
                260                 265                 270
Ile Thr Trp Asp Tyr Asp Gly Ile Gly Ser Asn Gly Lys Lys Val Asp
                275                 280                 285
His Asp Lys Phe Leu Asp Ala Glu Lys His Tyr Leu Pro Lys Thr
        290                 295                 300
Tyr Thr Phe Asp Asn Gly Thr Phe Ile Ile Arg Ala Gly Asp Lys Val
305                 310                 315                 320
Ser Glu Glu Lys Ile Lys Arg Leu Tyr Trp Ala Ser Arg Glu Val Lys
                325                 330                 335
Ser Gln Phe His Arg Val Val Gly Asn Asp Lys Ala Leu Glu Val Gly
        340                 345                 350
Asn Ala Asp Asp Val Leu Thr Met Lys Ile Phe Asn Ser Pro Glu Glu
        355                 360                 365
Tyr Lys Phe Asn Thr Asn Ile Asn Gly Val Ser Thr Asp Asn Gly Gly
        370                 375                 380
Leu Tyr Ile Glu Pro Arg Gly Thr Phe Tyr Thr Glu Arg Thr Pro
385                 390                 395                 400
Gln Gln Ser Ile Phe Ser Leu Glu Glu Leu Phe Arg His Glu Tyr Thr
                405                 410                 415
His Tyr Leu Gln Ala Arg Tyr Leu Val Asp Gly Leu Trp Gly Gln Gly
        420                 425                 430
Pro Phe Tyr Glu Lys Asn Arg Leu Thr Trp Phe Asp Glu Gly Thr Ala
        435                 440                 445
```

-continued

Glu Phe Phe Ala Gly Ser Thr Arg Thr Ser Gly Val Leu Pro Arg Lys
450                 455                 460

Ser Ile Leu Gly Tyr Leu Ala Lys Asp Lys Val Asp His Arg Tyr Ser
465                 470                 475                 480

Leu Lys Lys Thr Leu Asn Ser Gly Tyr Asp Asp Ser Asp Trp Met Phe
                485                 490                 495

Tyr Asn Tyr Gly Phe Ala Val Ala His Tyr Leu Tyr Glu Lys Asp Met
            500                 505                 510

Pro Thr Phe Ile Lys Met Asn Lys Ala Ile Leu Asn Thr Asp Val Lys
        515                 520                 525

Ser Tyr Asp Glu Ile Ile Lys Lys Leu Ser Asp Ala Asn Lys Asn
530                 535                 540

Thr Glu Tyr Gln Asn His Ile Gln Glu Leu Ala Asp Lys Tyr Gln Gly
545                 550                 555                 560

Ala Gly Ile Pro Leu Val Ser Asp Asp Tyr Leu Lys Asp His Gly Tyr
            565                 570                 575

Lys Lys Ala Ser Glu Val Tyr Ser Glu Ile Ser Lys Ala Ala Ser Leu
                580                 585                 590

Thr Asn Thr Ser Val Thr Ala Glu Lys Ser Gln Tyr Phe Asn Thr Phe
        595                 600                 605

Thr Leu Arg Gly Thr Tyr Thr Gly Glu Thr Ser Lys Gly Glu Phe Lys
610                 615                 620

Asp Trp Asp Glu Met Ser Lys Lys Leu Asp Gly Thr Leu Glu Ser Leu
625                 630                 635                 640

Ala Lys Asn Ser Trp Ser Gly Tyr Lys Thr Leu Thr Ala Tyr Phe Thr
                645                 650                 655

Asn Tyr Arg Val Thr Ser Asp Asn Lys Val Gln Tyr Asp Val Val Phe
            660                 665                 670

His Gly Val Leu Thr Asp Asn Ala Asp Ile Ser Asn Asn Lys Ala Pro
        675                 680                 685

Ile Ala Lys Val Thr Gly Pro Ser Thr Gly Ala Val Gly Arg Asn Ile
690                 695                 700

Glu Phe Ser Gly Lys Asp Ser Lys Asp Glu Asp Gly Lys Ile Val Ser
705                 710                 715                 720

Tyr Asp Trp Asp Phe Gly Asp Gly Ala Thr Ser Arg Gly Lys Asn Ser
                725                 730                 735

Val His Ala Tyr Lys Lys Ala Gly Thr Tyr Asn Val Thr Leu Lys Val
            740                 745                 750

Thr Asp Asp Lys Gly Ala Thr Ala Thr Glu Ser Phe Thr Ile Glu Ile
        755                 760                 765

Lys Asn Glu Asp Thr Thr Thr Pro Ile Thr Lys Glu Met Glu Pro Asn
770                 775                 780

Asp Asp Ile Lys Glu Ala Asn Gly Pro Ile Val Glu Gly Val Thr Val
785                 790                 795                 800

Lys Gly Asp Leu Asn Gly Ser Asp Ala Asp Thr Phe Tyr Phe Asp
                805                 810                 815

Val Lys Glu Asp Gly Asp Val Thr Ile Glu Leu Pro Tyr Ser Gly Ser
            820                 825                 830

Ser Asn Phe Thr Trp Leu Val Tyr Lys Glu Gly Asp Asp Gln Asn His
        835                 840                 845

Ile Ala Ser Gly Ile Asp Lys Asn Asn Ser Lys Val Gly Thr Phe Lys
850                 855                 860

Ser Thr Lys Gly Arg His Tyr Val Phe Ile Tyr Lys His Asp Ser Ala

```
            865                 870                 875                 880
        Ser Asn Ile Ser Tyr Ser Leu Asn Ile Lys Gly Leu Gly Asn Glu Lys
                        885                 890                 895

Leu Lys Glu Lys Glu Asn Asn Asp Ser Ser Asp Lys Ala Thr Val Ile
                        900                 905                 910

Pro Asn Phe Asn Thr Thr Met Gln Gly Ser Leu Leu Gly Asp Asp Ser
                        915                 920                 925

Arg Asp Tyr Tyr Ser Phe Glu Val Lys Glu Gly Glu Val Asn Ile
                        930                 935                 940

Glu Leu Asp Lys Lys Asp Glu Phe Gly Val Thr Trp Thr Leu His Pro
        945                 950                 955                 960

Glu Ser Asn Ile Asn Asp Arg Ile Thr Tyr Gly Gln Val Asp Gly Asn
                        965                 970                 975

Lys Val Ser Asn Lys Val Lys Leu Arg Pro Gly Lys Tyr Tyr Leu Leu
                        980                 985                 990

Val Tyr Lys Tyr Ser Gly Ser Gly Asn Tyr Glu Leu Arg Val Asn Lys
                        995                 1000                1005
```

<210> SEQ ID NO 2
<211> LENGTH: 981
<212> TYPE: PRT
<213> ORGANISM: Artificial Sequence
<220> FEATURE:
<223> OTHER INFORMATION: Synthetic Construct

<400> SEQUENCE: 2

```
        Val Gln Asn Glu Ser Lys Arg Tyr Thr Val Ser Tyr Leu Lys Thr Leu
        1               5                   10                  15

Asn Tyr Tyr Asp Leu Val Asp Leu Leu Val Lys Thr Glu Ile Glu Asn
                        20                  25                  30

Leu Pro Asp Leu Phe Gln Tyr Ser Ser Asp Ala Lys Glu Phe Tyr Gly
                        35                  40                  45

Asn Lys Thr Arg Met Ser Phe Ile Met Asp Glu Ile Gly Arg Arg Ala
                        50                  55                  60

Pro Gln Tyr Thr Glu Ile Asp His Lys Gly Ile Pro Thr Leu Val Glu
        65                  70                  75                  80

Val Val Arg Ala Gly Phe Tyr Leu Gly Phe His Asn Lys Glu Leu Asn
                        85                  90                  95

Glu Ile Asn Lys Arg Ser Phe Lys Glu Arg Val Ile Pro Ser Ile Leu
                        100                 105                 110

Ala Ile Gln Lys Asn Pro Asn Phe Lys Leu Gly Thr Glu Val Gln Asp
                        115                 120                 125

Lys Ile Val Ser Ala Thr Gly Leu Leu Ala Gly Asn Glu Thr Ala Pro
                        130                 135                 140

Pro Glu Val Val Asn Asn Phe Thr Pro Ile Leu Gln Asp Cys Ile Lys
        145                 150                 155                 160

Asn Ile Asp Arg Tyr Ala Leu Asp Asp Leu Lys Ser Lys Ala Leu Phe
                        165                 170                 175

Asn Val Leu Ala Ala Pro Thr Tyr Asp Ile Thr Glu Tyr Leu Arg Ala
                        180                 185                 190

Thr Lys Glu Lys Pro Glu Asn Thr Pro Trp Tyr Gly Lys Ile Asp Gly
                        195                 200                 205

Phe Ile Asn Glu Leu Lys Lys Leu Ala Leu Tyr Gly Lys Ile Asn Asp
                        210                 215                 220

Asn Asn Ser Trp Ile Ile Asp Asn Gly Ile Tyr His Ile Ala Pro Leu
```

```
                225                 230                 235                 240
Gly Lys Leu His Ser Asn Asn Lys Ile Gly Ile Glu Thr Leu Thr Glu
                    245                 250                 255

Val Met Lys Val Tyr Pro Tyr Leu Ser Met Gln His Leu Gln Ser Ala
                    260                 265                 270

Asp Gln Ile Lys Arg His Tyr Asp Ser Lys Asp Ala Glu Gly Asn Lys
                    275                 280                 285

Ile Pro Leu Asp Lys Phe Lys Lys Gly Lys Glu Lys Tyr Cys Pro
290                 295                 300

Lys Thr Tyr Thr Phe Asp Asp Gly Lys Val Ile Lys Ala Gly Ala
305                 310                 315                 320

Arg Val Glu Glu Glu Lys Val Lys Arg Leu Tyr Trp Ala Ser Lys Glu
                    325                 330                 335

Val Asn Ser Gln Phe Phe Arg Val Tyr Gly Ile Asp Lys Pro Leu Glu
                    340                 345                 350

Glu Gly Asn Pro Asp Asp Ile Leu Thr Met Val Ile Tyr Asn Ser Pro
                    355                 360                 365

Glu Glu Tyr Lys Leu Asn Ser Val Leu Tyr Gly Tyr Asp Thr Asn Asn
                    370                 375                 380

Gly Gly Met Tyr Ile Glu Pro Glu Gly Thr Phe Phe Thr Tyr Glu Arg
385                 390                 395                 400

Glu Ala Gln Glu Ser Thr Tyr Thr Leu Glu Glu Leu Phe Arg His Glu
                    405                 410                 415

Tyr Thr His Tyr Leu Gln Gly Arg Tyr Ala Val Pro Gly Gln Trp Gly
                    420                 425                 430

Arg Thr Lys Leu Tyr Asp Asn Asp Arg Leu Thr Trp Tyr Glu Glu Gly
                    435                 440                 445

Gly Ala Glu Leu Phe Ala Gly Ser Thr Arg Thr Ser Gly Ile Leu Pro
                    450                 455                 460

Arg Lys Ser Ile Val Ser Asn Ile His Asn Thr Thr Arg Asn Asn Arg
465                 470                 475                 480

Tyr Lys Leu Ser Asp Thr Val His Ser Lys Tyr Gly Ala Ser Phe Glu
                    485                 490                 495

Phe Tyr Asn Tyr Ala Cys Met Phe Met Asp Tyr Met Tyr Asn Lys Asp
                    500                 505                 510

Met Gly Ile Leu Asn Lys Leu Asn Asp Leu Ala Lys Asn Asn Asp Val
                    515                 520                 525

Asp Gly Tyr Asp Asn Tyr Ile Arg Asp Leu Ser Ser Asn Tyr Ala Leu
                    530                 535                 540

Asn Asp Lys Tyr Gln Asp His Met Gln Glu Arg Ile Asp Asn Tyr Glu
545                 550                 555                 560

Asn Leu Thr Val Pro Phe Val Ala Asp Asp Tyr Leu Val Arg His Ala
                    565                 570                 575

Tyr Lys Asn Pro Asn Glu Ile Tyr Ser Glu Ile Ser Glu Val Ala Lys
                    580                 585                 590

Leu Lys Asp Ala Lys Ser Glu Val Lys Lys Ser Gln Tyr Phe Ser Thr
                    595                 600                 605

Phe Thr Leu Arg Gly Ser Tyr Thr Gly Gly Ala Ser Lys Gly Lys Leu
                    610                 615                 620

Glu Asp Gln Lys Ala Met Asn Lys Phe Ile Asp Asp Ser Leu Lys Lys
625                 630                 635                 640

Leu Asp Thr Tyr Ser Trp Ser Gly Tyr Lys Thr Leu Thr Ala Tyr Phe
                    645                 650                 655
```

Thr Asn Tyr Lys Val Asp Ser Ser Asn Arg Val Thr Tyr Asp Val Val
         660                 665                 670

Phe His Gly Tyr Leu Pro Asn Glu Gly Asp Ser Lys Asn Ser Leu Pro
         675                 680                 685

Tyr Gly Lys Ile Asn Gly Thr Tyr Lys Gly Thr Glu Lys Glu Lys Ile
         690                 695                 700

Lys Phe Ser Ser Glu Gly Ser Phe Asp Pro Asp Gly Lys Ile Val Ser
705                 710                 715                 720

Tyr Glu Trp Asp Phe Gly Asp Gly Asn Lys Ser Asn Glu Glu Asn Pro
                 725                 730                 735

Glu His Ser Tyr Asp Lys Val Gly Thr Tyr Thr Val Lys Leu Lys Val
                 740                 745                 750

Thr Asp Asp Lys Gly Glu Ser Ser Val Ser Thr Thr Ala Glu Ile
                 755                 760                 765

Lys Asp Leu Ser Glu Asn Lys Leu Pro Val Ile Tyr Met His Val Pro
         770                 775                 780

Lys Ser Gly Ala Leu Asn Gln Lys Val Val Phe Tyr Gly Lys Gly Thr
785                 790                 795                 800

Tyr Asp Pro Asp Gly Ser Ile Ala Gly Tyr Gln Trp Asp Phe Gly Asp
                 805                 810                 815

Gly Ser Asp Phe Ser Ser Glu Gln Asn Pro Ser His Val Tyr Thr Lys
                 820                 825                 830

Lys Gly Glu Tyr Thr Val Thr Leu Arg Val Met Asp Ser Ser Gly Gln
                 835                 840                 845

Met Ser Glu Lys Thr Met Lys Ile Lys Ile Thr Asp Pro Val Tyr Pro
850                 855                 860

Ile Gly Thr Glu Lys Glu Pro Asn Asn Ser Lys Glu Thr Ala Ser Gly
865                 870                 875                 880

Pro Ile Val Pro Gly Ile Pro Val Ser Gly Thr Ile Glu Asn Thr Ser
                 885                 890                 895

Asp Gln Asp Tyr Phe Tyr Phe Asp Val Ile Thr Pro Gly Glu Val Lys
                 900                 905                 910

Ile Asp Ile Asn Lys Leu Gly Tyr Gly Gly Ala Thr Trp Val Val Tyr
         915                 920                 925

Asp Glu Asn Asn Ala Val Ser Tyr Ala Thr Asp Asp Gly Gln Asn
         930                 935                 940

Leu Ser Gly Lys Phe Lys Ala Asp Lys Pro Gly Arg Tyr Tyr Ile His
945                 950                 955                 960

Leu Tyr Met Phe Asn Gly Ser Tyr Met Pro Tyr Arg Ile Asn Ile Glu
                 965                 970                 975

Gly Ser Val Gly Arg
         980

<210> SEQ ID NO 3
<211> LENGTH: 3357
<212> TYPE: DNA
<213> ORGANISM: Artificial Sequence
<220> FEATURE:
<223> OTHER INFORMATION: Synthetic Construct

<400> SEQUENCE: 3
atgaaaaaaa atattttaaa gattcttatg gatagttatt ctaaagaatc taaaattcaa      60
actgtacgta gggttacgag tgtatcactt ttagcggtat atcttactat gaatacttca     120
agtttagttt tagcaaaacc aatagaaaat actaatgata ctagtataaa aaatgtggag     180

```
aaattaagaa atgctccaaa tgaagagaat agtaaaaagg tagaagatag taaaaatgat    240
aaggtagaac atgtgaaaaa tatagaagag gcaaaggttg agcaagttgc acccgaagta    300
aaatctaaat caactttaag aagtgcttct atagcgaata ctaattctga gaaatatgat    360
tttgagtatt taaatggttt gagctatact gaacttacaa atttaattaa aaatataaag    420
tggaatcaaa ttaatggttt atttaattat agtacaggtt ctcaaaagtt ctttggagat    480
aaaaatcgtg tacaagctat aattaatgct ttacaagaaa gtggaagaac ttacactgca    540
aatgatatga agggtataga aactttcact gaggttttaa gagctggttt ttatttaggg    600
tactataatg atggtttatc ttatttaaat gatagaaact tccaagataa atgtataccct   660 gcaatgattg caattcaaaa aaatcctaac tttaagctag gaactgcagt tcaagatgaa    720
gttataactt ctttaggaaa actaatagga atgcttctg ctaatgctga agtagttaat     780
aattgtgtac cagttctaaa acaatttaga gaaaacttaa atcaatatgc tcctgattac    840
gttaaaggaa cagctgtaaa tgaattaatt aaaggtattg aattcgattt ttctggtgct    900
gcatatgaaa aagatgttaa gacaatgcct tggtatggaa aaattgatcc atttataaat    960
gaacttaagg ccttaggtct atatggaaat ataacaagtg caactgagtg ggcatctgat   1020
gttggaatat actatttaag taaattcggt ctttactcaa ctaaccgaaa tgacatagta   1080
cagtcacttg aaaaggctgt agatatgtat aagtatggta aaatagcctt tgtagcaatg   1140
gagagaataa cttgggatta tgatgggatt ggttctaatg gtaaaaaggt ggatcacgat   1200
aagttcttag atgatgctga aaacattat ctgccaaaga catatacttt tgataatgga    1260
acctttatta taagagcagg ggataaggta tccgaagaaa aaataaaaag gctatattgg   1320
gcatcaagag aagtgaagtc tcaattccat agagtagttg gcaatgataa agctttagag   1380
gtgggaaatg ccgatgatgt tttaactatg aaaatattta tagcccaga gaatataaa     1440 tttaatacca atataaatgg tgtaagcact gataatggtg gtctatatat agaaccaaga   1500
gggactttct acacttatga gagaacacct caacaaagta tatttagtct tgaagaattg   1560
tttagacatg aatatactca ctatttacaa gcgagatatc ttgtagatgg tttatggggg   1620
caaggtccat tttatgaaaa aaatagatta acttggtttg atgaaggtac agctgaattc   1680
tttgcaggat ctacccgtac atctggtgtt ttaccaagaa aatcaatatt aggatatttg   1740
gctaaggata aagtagatca tagatactca ttaaagaaga ctcttaattc agggtatgat   1800
gacagtgatt ggatgttcta taattatgga tttgcagttg cacattaccct atatgaaaaa   1860 gatatgccta catttattaa gatgaataaa gctatattga atacagatgt gaaatcttat   1920
gatgaaataa taaaaaaatt aagtgatgat gcaaataaaa atacagaata tcaaaaccat   1980
attcaagagt tagcagataa atatcaagga gcaggcatac ctctagtatc agatgattac   2040
ttaaaagatc atggatataa gaaagcatct gaagtatatt ctgaaatttc aaaagctgct   2100
tctcttacaa acactagtgt aacagcagaa aaatctcaat atttttaacac attcacttta   2160 agaggaactt atacaggtga aacttctaaa ggtgaattta agattgggga tgaaatgagt   2220
aaaaaattag atggaacttt ggagtccctt gctaaaaatt cttggagtgg atacaaaact   2280
ttaacagcat acttacgaa ttatagagtt acaagcgata taaagttca atatgatgta     2340 gttttccatg gggtttttaac agataatgcg gatattagta acaataaggc tccaatagca   2400
aaggtaactg gaccaagcac tggtgctgta ggaagaaata ttgaatttag tggaaaagat   2460
agtaaagatg aagatggtaa aatagtatca tatgattggg attttggcga tggtgcaact   2520
```

| | | |
|---|---|---|
| agtagaggca aaaattcagt acatgcttac aaaaaagcag gaacatataa tgttacatta | 2580 | |
| aaagtaactg acgataaggg tgcaacagct acagaaagct ttactataga aataaagaac | 2640 | |
| gaagatacaa caacacctat aactaaagaa atggaaccta atgatgatat aaaagaggct | 2700 | |
| aatggtccaa tagttgaagg tgttactgta aaaggtgatt taaatggttc tgatgatgct | 2760 | |
| gataccttct attttgatgt aaaagaagat ggtgatgtta caattgaact tccttattca | 2820 | |
| gggtcatcta atttcacatg gttagtttat aaagagggag acgatcaaaa ccatattgca | 2880 | |
| agtggtatag ataagaataa ctcaaaagtt ggaacattta atctacaaa aggaagacat | 2940 | |
| tatgtgttta tatataaaca cgattctgct tcaaatatat cctattcttt aaacataaaa | 3000 | |
| ggattaggta acgagaaatt gaaggaaaaa gaaaataatg attcttctga taaagctaca | 3060 | |
| gttataccaa atttcaatac cactatgcaa ggttcacttt taggtgatga ttcaagagat | 3120 | |
| tattattctt ttgaggttaa ggaagaaggc gaagttaata tagaactaga taaaaaggat | 3180 | |
| gaatttggtg taacatggac actacatcca gagtcaaata ttaatgacag aataacttac | 3240 | |
| ggacaagttg atggtaataa ggtatctaat aaagttaaat taagaccagg aaaatattat | 3300 | |
| ctacttgttt ataaatactc aggatcagga actatgagt taagggtaaa taaataa | 3357 | |

<210> SEQ ID NO 4
<211> LENGTH: 330
<212> TYPE: DNA
<213> ORGANISM: Artificial Sequence
<220> FEATURE:
<223> OTHER INFORMATION: Synthetic Construct

<400> SEQUENCE: 4

| | | |
|---|---|---|
| atgaaaaaaa atattttaaa gattcttatg gatagttatt ctaaagaatc taaaattcaa | 60 | |
| actgtacgta gggttacgag tgtatcactt ttagcggtat atcttactat gaatacttca | 120 | |
| agtttagttt tagcaaaacc aatagaaaat actaatgata ctagtataaa aaatgtggag | 180 | |
| aaattaagaa atgctccaaa tgaagagaat agtaaaaagg tagaagatag taaaaatgat | 240 | |
| aaggtagaac atgtgaaaaa tatagaagag gcaaaggttg agcaagttgc acccgaagta | 300 | |
| aaatctaaat caactttaag aagtgcttct | 330 | |

<210> SEQ ID NO 5
<211> LENGTH: 110
<212> TYPE: PRT
<213> ORGANISM: Artificial Sequence
<220> FEATURE:
<223> OTHER INFORMATION: Synthetic Construct

<400> SEQUENCE: 5

Met Lys Lys Asn Ile Leu Lys Ile Leu Met Asp Ser Tyr Ser Lys Glu
1               5                   10                  15

Ser Lys Ile Gln Thr Val Arg Arg Val Thr Ser Val Ser Leu Leu Ala
        20                  25                  30

Val Tyr Leu Thr Met Asn Thr Ser Ser Leu Val Leu Ala Lys Pro Ile
    35                  40                  45

Glu Asn Thr Asn Asp Thr Ser Ile Lys Asn Val Glu Lys Leu Arg Asn
50                  55                  60

Ala Pro Asn Glu Glu Asn Ser Lys Lys Val Glu Asp Ser Lys Asn Asp
65                  70                  75                  80

Lys Val Glu His Val Lys Asn Ile Glu Glu Ala Lys Val Glu Gln Val
                85                  90                  95

Ala Pro Glu Val Lys Ser Lys Ser Thr Leu Arg Ser Ala Ser

<210> SEQ ID NO 6
<211> LENGTH: 3066
<212> TYPE: DNA
<213> ORGANISM: Artificial Sequence
<220> FEATURE:
<223> OTHER INFORMATION: Synthetic Construct

<400> SEQUENCE: 6

| | | | | | |
|---|---|---|---|---|---|
| atgaaaagga | aatgtttatc | taaaaggctt | atgttagcta | taacaatggc | tacaatattt | 60 |
| acagtgaaca | gtacattacc | aatttatgca | gctgtagata | aaataatgc | aacagcagct | 120 |
| gtacaaaatg | aaagtaagag | gtatacagta | tcatatttaa | agactttaaa | ttattatgac | 180 |
| ttagtagatt | tgcttgttaa | gactgaaatt | gagaatttac | agaccttttt | tcagtatagt | 240 |
| tcagatgcaa | aagagttcta | tggaaataaa | actcgtatga | gctttatcat | ggatgaaatt | 300 |
| ggtagaaggg | cacctcagta | tacagagata | gatcataaag | gtattcctac | tttagtagaa | 360 |
| gttgtaagag | ctggatttta | cttaggattc | cataacaagg | aattgaatga | aataaacaag | 420 |
| aggtctttta | agaaagggt | aataccttct | atattagcaa | ttcaaaaaaa | tcctaatttt | 480 |
| aaactaggta | ctgaagttca | agataaaata | gtatctgcaa | caggactttt | agctggtaat | 540 |
| gaaacagcgc | ctccagaagt | tgtaaataat | tttacaccaa | tacttcaaga | ctgtataaag | 600 |
| aatatagaca | gatacgctct | tgatgattta | aagtcaaaag | cattatttaa | tgttttagct | 660 |
| gcacctacct | atgatataac | tgagtattta | agagctacta | agaaaaaacc | agaaaacact | 720 |
| ccttggtatg | gtaaaataga | tgggtttata | atgaacttaa | aaagttagc | tctttatgga | 780 |
| aaaataaatg | ataataactc | ttggataata | gataacggta | tatatcatat | agcaccttta | 840 |
| gggaagttac | atagcaataa | taaaatagga | atagaaactt | taacagaggt | tatgaaagtt | 900 |
| tatccttatt | taagtatgca | acatttacaa | tcagcagatc | aaattaagcg | tcattatgat | 960 |
| tcaaaagatg | ctgaaggaaa | caaaatacct | ttagataagt | ttaaaaagga | aggaaaagaa | 1020 |
| aaatactgtc | caaaaactta | tacatttgat | gatggaaaag | taataataaa | agctggtgct | 1080 |
| agagtagaag | aagaaaaagt | taaaagacta | tactgggcat | caaggaagt | taactctcaa | 1140 |
| ttctttagag | tatacggaat | agacaaacca | ttagaagaag | gtaatccaga | tgatatatta | 1200 |
| acaatggtta | tctacaacag | tcccgaagaa | tataaactca | atagtgttct | atacggatat | 1260 |
| gatactaata | atggtggtat | gtatatagag | ccagaaggaa | ctttcttcac | ctatgaaaga | 1320 |
| gaagctcaag | aaagcacata | cacattagaa | gaattattta | gacatgaata | tacacattat | 1380 |
| ttgcaaggaa | gatatgcagt | tccaggacaa | tggggaagaa | caaaacttta | tgacaatgat | 1440 |
| agattaactt | ggtatgaaga | aggtggagca | gaattatttg | caggttctac | tagaacttct | 1500 |
| ggaatattac | caagaaagag | tatagtatca | aatattcata | tacaacaag | aataatagaa | 1560 |
| tataagcttt | cagacactgt | tacattctaaa | atggtgcta | gttttgaatt | ctataattat | 1620 |
| gcatgtatgt | ttatggatta | tatgtataat | aaagatatgg | gtatattaaa | taaactaaat | 1680 |
| gatcttgcaa | aaaataatga | tgttgatgga | tatgataatt | atattagaga | tttaagttct | 1740 |
| aattatgctt | taaatgataa | atatcaagat | catatgcagg | agcgcataga | taattatgaa | 1800 |
| aatttaacag | tgccttttgt | agctgatgat | tatttagtaa | ggcatgctta | taagaaccct | 1860 |
| aatgaaattt | attctgaaat | atctgaagta | gcaaaattaa | aggatgctaa | gagtgaagtt | 1920 |
| aagaaatcac | aatattttag | tacctttact | ttgagaggta | gttacacagg | tggagcatct | 1980 |
| aagggggaaat | tagaagatca | aaaagcaatg | aataagttta | tagatgattc | acttaagaaa | 2040 |

-continued

```
ttagatacgt attcttggag tgggtataaa actttaactg cttatttcac taattataaa      2100
gttgactctt caaatagagt tacttatgat gtagtattcc acggatattt accaaacgaa      2160
ggtgattcca aaaattcatt acctatggc aagatcaatg gaacttacaa gggaacagag       2220
aaagaaaaaa tcaaattctc tagtgaaggc tctttcgatc cagatggtaa aatagtttct      2280
tatgaatggg atttcggaga tggtaataag agtaatgagg aaaatccaga gcattcatat     2340
gacaaggtag gaacttatac agtgaaatta aaagttactg atgacaaggg agaatcttca     2400
gtatctacta ctactgcaga ataaaggat ctttcagaaa ataaacttcc agttatatat      2460
atgcatgtac ctaaatccgg agccttaaat caaaagttg ttttctatgg aaaaggaaca      2520
tatgacccag atggatctat cgcaggatat caatgggact ttggtgatgg aagtgatttt     2580
agcagtgaac aaaacccaag ccatgtatat actaaaaaag gtaatatac tgtaacatta      2640 agagtaatgg atagtagtgg acaaatgagt gaaaaaacta tgaagattaa gattacagat    2700
ccggtatatc aataggcac tgaaaagaa ccaaataaca gtaaagaaac tgcaagtggt       2760
ccaatagtac caggtatacc tgttagtgga accatagaaa atacaagtga tcaagattat    2820
ttctattttg atgttataac accaggagaa gtaaaaatag atataaataa attagggtac    2880
ggaggagcta cttgggtagt atatgatgaa aataataatg cagtatctta tgccactgat   2940
gatgggcaaa atttaagtgg aaagtttaag gcagataaac caggtagata ttacatccat    3000
ctttacatgt taatggtag ttatatgcca tatagaatta atatagaagg ttcagtagga     3060
agataa                                                                 3066
```

<210> SEQ ID NO 7
<211> LENGTH: 120
<212> TYPE: DNA
<213> ORGANISM: Artificial Sequence
<220> FEATURE:
<223> OTHER INFORMATION: Synthetic Construct

<400> SEQUENCE: 7

```
atgaaaagga aatgtttatc taaaaggctt atgttagcta taacaatggc tacaatattt       60
acagtgaaca gtacattacc aatttatgca gctgtagata aaaataatgc aacagcagct     120
```

<210> SEQ ID NO 8
<211> LENGTH: 40
<212> TYPE: PRT
<213> ORGANISM: Artificial Sequence
<220> FEATURE:
<223> OTHER INFORMATION: Synthetic Construct

<400> SEQUENCE: 8

Met Lys Arg Lys Cys Leu Ser Lys Arg Leu Met Leu Ala Ile Thr Met
1               5                   10                  15

Ala Thr Ile Phe Thr Val Asn Ser Thr Leu Pro Ile Tyr Ala Ala Val
            20                  25                  30

Asp Lys Asn Asn Ala Thr Ala Ala
        35                  40